United States Patent
Chefd'hotel et al.

(10) Patent No.: US 8,121,379 B2
(45) Date of Patent: Feb. 21, 2012

(54) INTENSITY-BASED IMAGE REGISTRATION USING EARTH MOVER'S DISTANCE

(75) Inventors: Christophe Chefd'hotel, Princeton, NJ (US); Guillaume Bousquet, Lawrenceville, NJ (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 1048 days.

(21) Appl. No.: 11/805,218

(22) Filed: May 22, 2007

(65) Prior Publication Data

US 2008/0039706 A1   Feb. 14, 2008

Related U.S. Application Data

(60) Provisional application No. 60/836,596, filed on Aug. 9, 2006.

(51) Int. Cl.
   *G06K 9/00* (2006.01)
(52) U.S. Cl. ...................................... 382/132
(58) Field of Classification Search .............. 382/190, 382/159, 128, 131, 132
   See application file for complete search history.

(56) References Cited

U.S. PATENT DOCUMENTS

| | | | |
|---|---|---|---|
| 6,243,133 B1 | 6/2001 | Spaulding | |
| 6,711,285 B2 | 3/2004 | Noguchi | |
| 7,064,769 B2 | 6/2006 | Speigle | |
| 7,130,457 B2* | 10/2006 | Kaufman et al. | 382/128 |
| 2006/0023947 A1* | 2/2006 | Rising, III | 382/190 |
| 2006/0165277 A1* | 7/2006 | Shan et al. | 382/159 |

OTHER PUBLICATIONS

A. Chung et al., Multi-modal Image Registation by Minimising Kullback-Leibler Distance, Proceedings of the conference on Medical Image Computing and Computer-Assisted Intervention, II:525-532, 2002.
F. Mass et al., Multimodality Image Registration by Maximization of Mutual Information, IEEE Transactions on Medical Imaging, 16(2):187-198, 1997.
H. Ling and K. Okada, EMD-L1: An Efficient and Robust Algorithm for Comparing Histogram-Based Descriptors, Proceedings of the European Conference on Computer Vision, LNCS 3953, III:330-343, 2006.
Y. Rubner et al., A Metric for Distributions with Applications to Image Databases, Proceedings of the IEEE International Conference on Computer Vision, Bombay, India, 1998.
G. Studholme et al., Automated Three-Dimensional Registration of Magenetic Resonance and Positron Emission Tomorgraphy Brain Images by Multiresolution Optimization of Voxel Similarity Measures, Medical Physics, 24(1):25-35, 1997.
S. Wells et al., Multi-modal Volume Registration by Maximization of Mutual Information, Medical Image Analysis, 1(1):35-51, 1996.
Y. Rubner et al., The Earth Movers Distance as a Metric for Image Retrieval, Technical Report STAN-CS-TN-98-86, Stanford Computer Science Department, Sep. 1998, http://vision.stanford.edu/public/publication/rubner/rubner_Tr_98-pdf.

* cited by examiner

*Primary Examiner* — Claire X Wang
(74) *Attorney, Agent, or Firm* — Donald B. Paschburg

(57) ABSTRACT

A method of aligning image having the steps of obtaining a first image, the first image having a corresponding first data set, obtaining a second image, the second having a corresponding second data set; learning a joint intensity distribution from a pair of prealigned images, and aligning the first image and the second image by computing Earth Mover's Distance between their observed joint intensity distribution and the learned joint intensity distribution.

29 Claims, 19 Drawing Sheets

INTENSITY-BASED IMAGE REGISTRATION USING EARTH MOVER'S DISTANCE

CROSS-REFERENCE TO RELATED APPLICATIONS

This is a United States non-provisional application of U.S. provisional patent application Ser. No. 60/836,596 filed Aug. 9, 2006 by Christophe Chefd'hotel and Guillaume Bousquet, the entirety of which application is incorporated by reference herein.

FIELD OF THE INVENTION

The present invention relates to scanning evaluation methods and apparatus for medical devices. More specifically, the present invention relates to scanning methods and apparatus used to align two dimensional and three dimensional medical image scans and data using Earth Mover's Distance as a metric for the space of joint intensity distributions.

BACKGROUND INFORMATION

Medical imaging is increasingly being used for identification of medical problems for patients. Image registration is a key component of post-processing medical images. Image registration typically consists of finding a geometric transformation that aligns a pair of images or volumes. The geometric transformation can be used to compensate for motion, detect changes, or fuse complementary information provided by different acquisition devices. Proposed conventional methods for such transformations range from feature based techniques, that establish correspondences between geometric features extracted from images, to intensity-based approaches. In the case of intensity-based approaches, image registration is often formulated as an optimization problem, where best alignment is obtained by maximizing a measure of intensity similarity between homologous points of a reference image and a study image. In particular, statistical and information theoretic similarity measures have proven very effective in practice and can even solve multimodal registration problems.

The needs of patients varies from general investigative procedures to more evaluative procedures where precision is required. Thus, in some circumstances, great precision is required, for example, in vasculature investigation in the brain.

A potential application of such techniques is the alignment of brain image scans in Magnetic Resonance Image (MRI) or computer tomography (CT). For instance, these scans allow a three dimensional representation of the patients brain to enable the physician to more accurately guide the instrument in neurosurgery.

Currently, however, the conventional methods and apparatus used to attempt to align two images, for example using statistical methods based on Kullback-Leibler (KL) divergence, Mutual Information (MI) and Normalized Mutual Information (NMI) may not provide results that are accurate and consequently information that is available to medical professionals can be misleading. As patients may be evaluated with different types of scanning equipment, data scans from one machine do not necessarily correlate to data scans of other machines. The machines commonly used can differ in configuration so there is a need to provide an arrangement and method to align the data scans of the different machines in a timely and cost efficient manner.

There is a need, therefore, to provide a method and apparatus to allow two images or two data sets of images to be aligned in a highly accurate manner, such that continuity of data is attained.

There is also a need to provide a method and apparatus that is computationally compact and efficient.

There is also a need for a method and apparatus that will aid physicians and technicians in comparison of data values between data scan sets for translation, rotation, scaling and arbitrary non-rigid transformation.

There is a still further need to provide a method and apparatus that allows two images or two data sets of images from differing machines to be compared in a highly accurate manner such that continuity of data is attained, other than standardized evaluative methods, using Kullback-Leibler evaluative techniques.

There is a still further need to provide a method and apparatus to allow any set of images, other than those derived from medical imaging devices, to be compared to one another.

SUMMARY OF THE INVENTION

There is therefore and objective of the present invention to provide a method and apparatus to allow two images or two data sets of images to be aligned in a highly accurate manner, such that continuity of data is attained.

There is also an objective of the present invention to provide a method and apparatus that is computationally compact and efficient.

There is also an objective of the present invention to provide a method and apparatus that will aid physicians and technicians in comparison of data values between data scan sets for translation, rotation, scaling and arbitrary non-rigid transformation.

There is a still further objective of the present invention to provide a method and apparatus that allows two images or two data sets of images from differing machines to be compared in a highly accurate manner such that continuity of data is attained, other than standardized evaluative methods, using Kullback-Leibler evaluative techniques.

There is a still further objective of the present invention to provide a method and apparatus to allow any set of images, other than those derived from medical imaging devices, to be compared to one another.

The objectives of the present invention are achieved as illustrated and described.

A first exemplary embodiment of the invention provides a method of aligning at least two medical scan images, comprising the steps of obtaining a first medical scan image, the first medical scan image having a corresponding first data set, obtaining a second medical scan image, the second medical scan image having a corresponding second data set, calculating a joint density, with marginals from the first medical scan image and the second medical scan image, comparing the first medical scan image with the second medical scan image using an Earth Mover's Distance, and
aligning the first medical scan image with the second medical scan image with results obtained from the comparing of the first medical scan image with the second medical scan image using the Earth Mover's Distance.

In this exemplary embodiment, the method provides that the image intensity values of the first data set and image intensity values of the second data set are used in estimating the joint density of the first medical scan image and the second medical scan image. The method may also be accomplished such that the first medical scan image and the second medical scan image are magnetic resonance images or computer tomography scan images.

Another exemplary embodiment of the present invention provides a method of aligning at least two images, having the steps of obtaining a first image, the first image having a corresponding first data set, obtaining a second image, the second having a corresponding second data set, learning a joint intensity distribution from a pair of prealigned images, and aligning the first image and the second image by computing Earth Mover's Distance between their observed joint intensity distribution and the learned joint intensity distribution.

This exemplary embodiment may be accomplished such that the step of aligning the first image and the second image by computing Earth Mover's Distance between their observed joint intensity distribution and the learned joint intensity distribution is accomplished using an Earth Mover's Distance induced through a formula of $$\epsilon_b(I_1, I_{2,T}) = EMD_{L_1}(p_{x_1, x_2, T}, p_0).$$

Additionally, the method may be accomplished such that the image intensity values of the first data set and image intensity values of the second data set are used in calculating the observed joint intensity distribution of the first medical scan image and the second medical scan image.

In this exemplary embodiment, the first image and the second image may be magnetic resonance images or computer tomography scans.

The present invention also provides a program storage device readable by machine, tangibly embodying a program of instructions executable by the machine to perform method steps for aligning at least two medical scan images, comprising the steps of obtaining a first medical scan image, the first medical scan image having a corresponding first data set, obtaining a second medical scan image, the second medical scan image having a corresponding second data set, calculating a joint density, with marginals from the first medical scan image and the second medical scan image, comparing the first medical scan image with the second medical scan image using an Earth Mover's Distance, and aligning the first medical scan image with the second medical scan image with results obtained from the comparing of the first medical scan image with the second medical scan image using the Earth Mover's Distance.

The present invention also provides a program storage device readable by machine, tangibly embodying a program of instructions executable by the machine to perform method steps for aligning at least two medical scan images, comprising: obtaining a first image, the first image having a corresponding first data set, obtaining a second image, the second having a corresponding second data set, learning a joint intensity distribution from a pair of prealigned images, and aligning the first image and the second image by computing Earth Mover's Distance between their observed joint intensity distribution and the learned joint intensity distribution.

The present invention also provides a method of aligning at least two images, comprising the steps of obtaining a first image, the first image having a corresponding first data set, obtaining a second image, the second having a corresponding second data set, and aligning the first image and the second image by computing Earth Mover's Distance between their observed joint intensity distribution and the product of its marginals.

DETAILED DESCRIPTION

Figure 1:
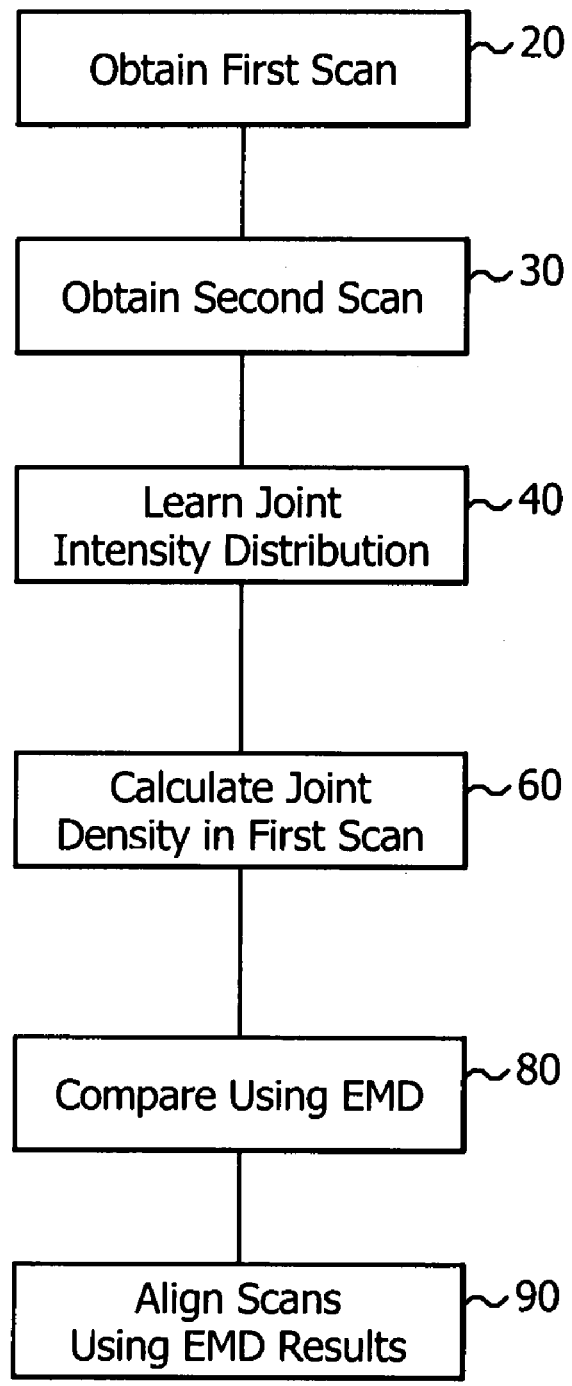
FIG. 1 is an exemplary method using Earth Mover's Distance as a metric for intensity-based image registration in conformance with the present invention.

The present invention relates to aligning scanned images. In the exemplary embodiment provided in the present invention, two different intensity values of two images $I_1$ and $I_{2,T}$ are modeled by random variables $X_1$ and $X_2$. For the purposes of the exemplary embodiment of the method, $I_1$ corresponds to a reference (known) image and T is a spatial transformation applied to a study image $I_2$ to produce a transformed image, $I_{2,T}$.

For any given pixel location x, $I_{2,T}(x) = I_2(T(x))$. The value T belongs to an arbitrary class K of mappings ranging from rigid transformations to high-dimensional nonrigid deformations. Images are acquired on a finite sampling grid and values of $I_{2,T}$ are obtained from the study image $I_2$ by interpolation. The joint density of the pair $(X_1, X_{2,T})$ is denoted, $p_{x_1, x_{2,T}}$ with marginals $p_{x_1} p_{x_{2,T}}$. The intensities of $I_1$ and $I_{2,T}$ and are a finite set of values. The joint intensity distribution and its marginals are represented by normalized histograms.

As opposed to the KL, MI and NMI evaluation techniques, the Earth Mover's Distance is used to allow for better evaluation of histogram similarity independently of quantization effects and deformations of the feature space. Earth Mover's Distance is referred to as a "cross-bin" distance as opposed to "bin to bin" distances such as used in KL. When applied to normalized histograms, Earth Mover's Distance is a discrete version of the Wasserstein metric in probability theory. This metric is the solution of an optimal mass transportation problem. The Earth Mover's Distance corresponds to the cost of optimally transporting one distribution into the other given a ground distance. The ground distance is typically derived from an $L_p$ norm, for instance $d_p(x,y) = \|x-y\|_p$ where (p=2 yields the Euclidean distance). More formally, given two normalized histograms $h_1$ and $h_2$, whose ith bins are centered at locations $x_i$ and $y_i$, respectively, Earth Mover's Distance is defined by $$EMD(h_1, h_2) = \min_{f_{i,j}} \sum_{i,j} f_{i,j} d_p(x_i, y_j)$$

Subject to the following constraints:

$$f_{i,j} \geq 0, \forall i, j,$$

$$\sum_j f_{i,j} = h_1(i), \forall i,$$

$$\sum_i f_{i,j} = h_2(j), \forall j.$$

These values $f_{i,j}$ can be seen as elementary flows transporting elements of $h_1$ and $h_2$ (or $h_2$ to $h_1$). This approach generalizes to multidimensional histograms such as joint intensity distributions. When the ground distance is arbitrary, the optimal solution to the linear programming problem is given by a transportation simplex algorithm.

With this definition, two Earth Mover's distance based similarity measures are provided. The first measure is:

$$\epsilon_a(I_1, I_2, T) = EMD_{L_1}(p_{x_1, x_2, T}, p_{x_1} p_{x_2, T}).$$

This value is maximized to achieve registration. The second is used when a learned joint intensity distribution $p_0$ is available.

$$\epsilon_b(I_1, I_2, T) = EMD_{L_1}(p_{x_1, x_2, T}, p_0).$$

$\epsilon_b$ is minimized in order to align a pair of images. The implementation of these new measures raises several practical challenges. Computing Earth Mover's Distance for a pair of joint distribution and histograms involves solving a linear programming problem. The registration process requires multiple evaluations of Earth Mover's Distance on two dimensional histograms. To accomplish this, an algorithm providing the following 6 steps of pseudo-code allows for a compact solution.

Using this approach, the linear programming problem can be drastically simplified in order to get a much more efficient simplex algorithm. Computation times make the use of $EMD_L$ possible for registration purposes.

Referring to FIG. 1 the method 10 of aligning at least two medical scan images is presented. A first medical scan image is obtained 20, the first medical scan image having a corresponding first data set. Next, a second medical scan image is obtained 30, the second medical scan image having a corresponding second data set. Next, a joint intensity distribution is learned 40 between two medical scan images. In the exemplary embodiment, two images from a patient are used, different than the first and second medical scan images. Following this step, a joint density is calculated, with marginals in the first medical scan image and second medical scan image 60. Following this step, the first medical scan image is compared with the second medical scan image using an Earth Mover's Distance 80. Finally, the first medical scan image is aligned with the second medical scan image with results obtained from the comparing of the first medical scan image with the second medical scan image using the Earth Mover's Distance 90. The above order of steps may also be augmented if a a learned joint intensity distribution is known $p_o$. For this instance, the images may be pre-aligned and the factor $$\epsilon_b(I_1, I_2, T) = EMD_{L_1}(p_{x_1, x_2, T}, p_0).$$

minimized to align the images as completely as possible.

Figure 5:
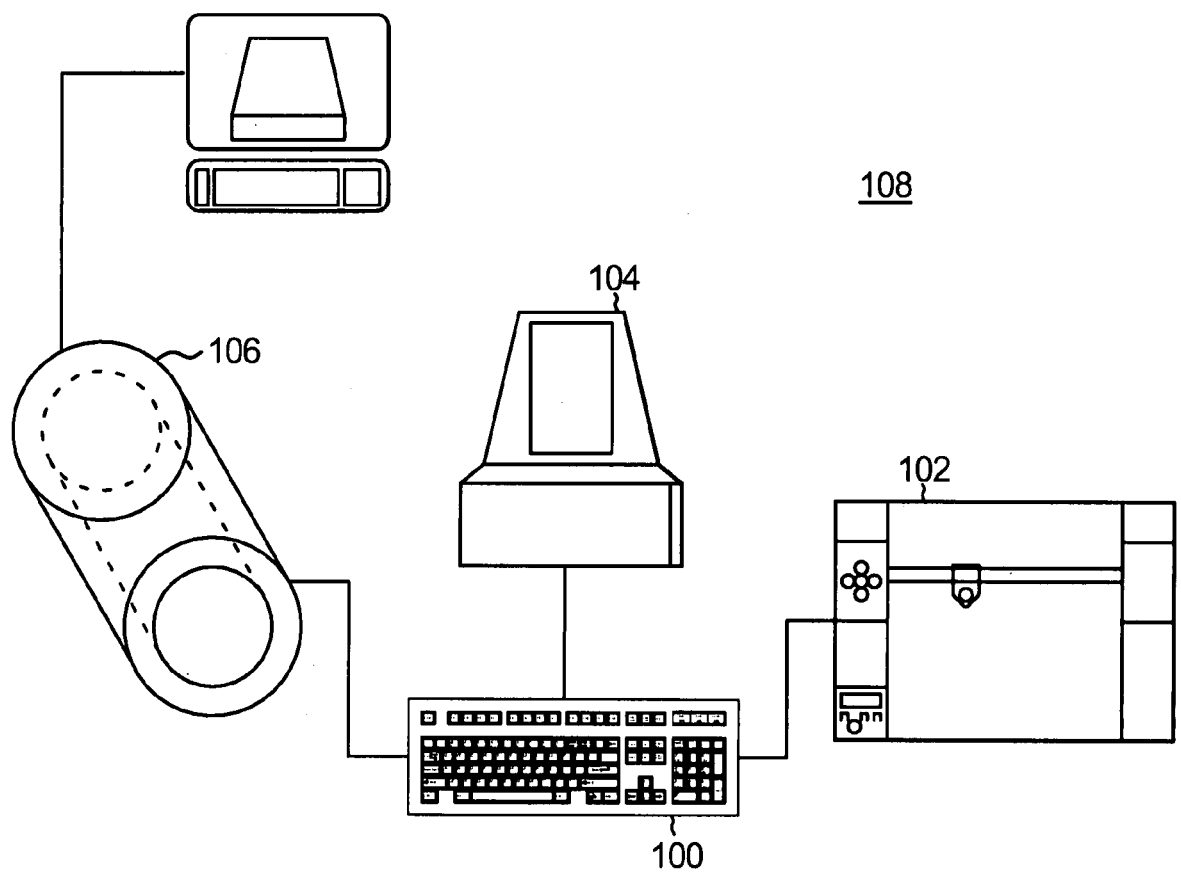
FIG. 5 is a exemplary embodiment of the arrangement for performing the method of FIG. 1.

Referring to FIG. 5, an exemplary embodiment of an arrangement 108 of conducting analysis for alignment of medical scan images is presented. A computer 100 is used for the analysis of the data sets. The computer 100 is provided with an input capability to allow MRI scan data, for example, to be accepted into the computer 100. A Graphical User Interface (GUI) may be used by the physician/technician for easing input of the information into the computer 100. The computer 100 is connected, in the exemplary embodiment, to two output devices 102, 104. In the illustrated embodiment of the present invention, a first output device is a printer 102 that can superimpose the data sets for viewing. Additionally, a monitor 104 is provided such that the visual images of the superimposed data sets can be used by physicians. The computer 100 is connected to a data source input, in this case, an MRI machine 106, however other data acquisition systems, such as CT scanning devices may be used.

Exemplary Embodiment

Experiments with two pairs of Magnetic Resonance brain images were performed. The first pair was acquired from a volunteer with a Siemens Magnetom Avanto 1.5T machine. One of the datasets was obtained with a T2-weighted HASTE sequence (matrix size 512×384, 22 slices, voxel size of 0.45× 0.45×5 $mm^3$) and the other with a T1 weighted Spin-Echo sequence (matrix size 192×192, 36 slices, voxel size of 1.2× 1.2×3 $mm^3$) A volunteer was asked to move his head after the first acquisition to simulate a misalignment of large amplitude. A pair of simulated T1 and T2 weighted MR images from a database are used to generate ground truth data and measure registration errors. The database had a volume size of 181×217×181 and isotropic voxels (1 $mm^3$). Their intensity non-uniformity was set to 20%. The noise level of the T1 and T2 weighted images was set to 3% and 9% respectively.

In all registration experiments, the number of quantization levels was set to 16. This value was chosen empirically and provides a good compromise between registration accuracy and computational efficiency. Joint histograms were computed using partial volume interpolation. In the rigid registration experiments we applied a multi-resolution hill-climbing optimization strategy. With a 3 GHz microprocessor, the evaluation $EMD_L$ takes on average 1 ms for histograms of size $16^2$. This computation time increases dramatically to 15 ms for a size of $32^2$ and up to 313 ms for $64^2$.

Figure 2A:
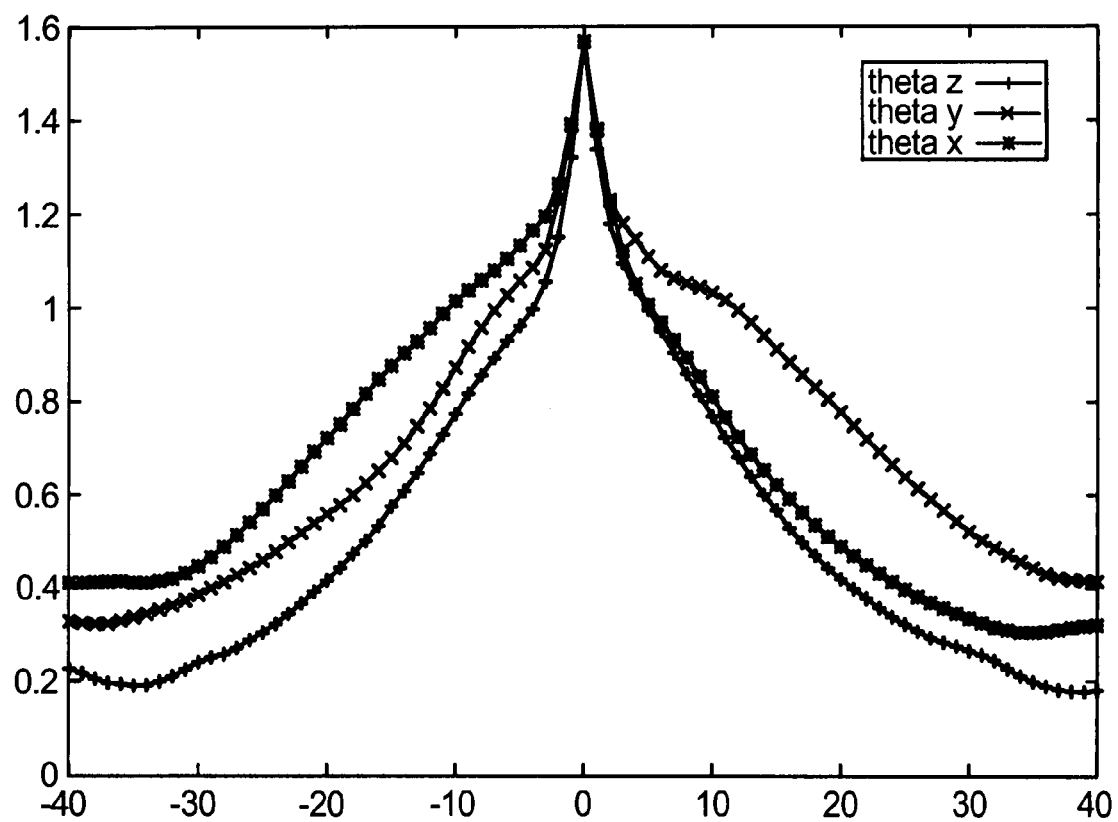
FIG. 2A is a graph showing Ea with respect to rotation.
Figure 2B:
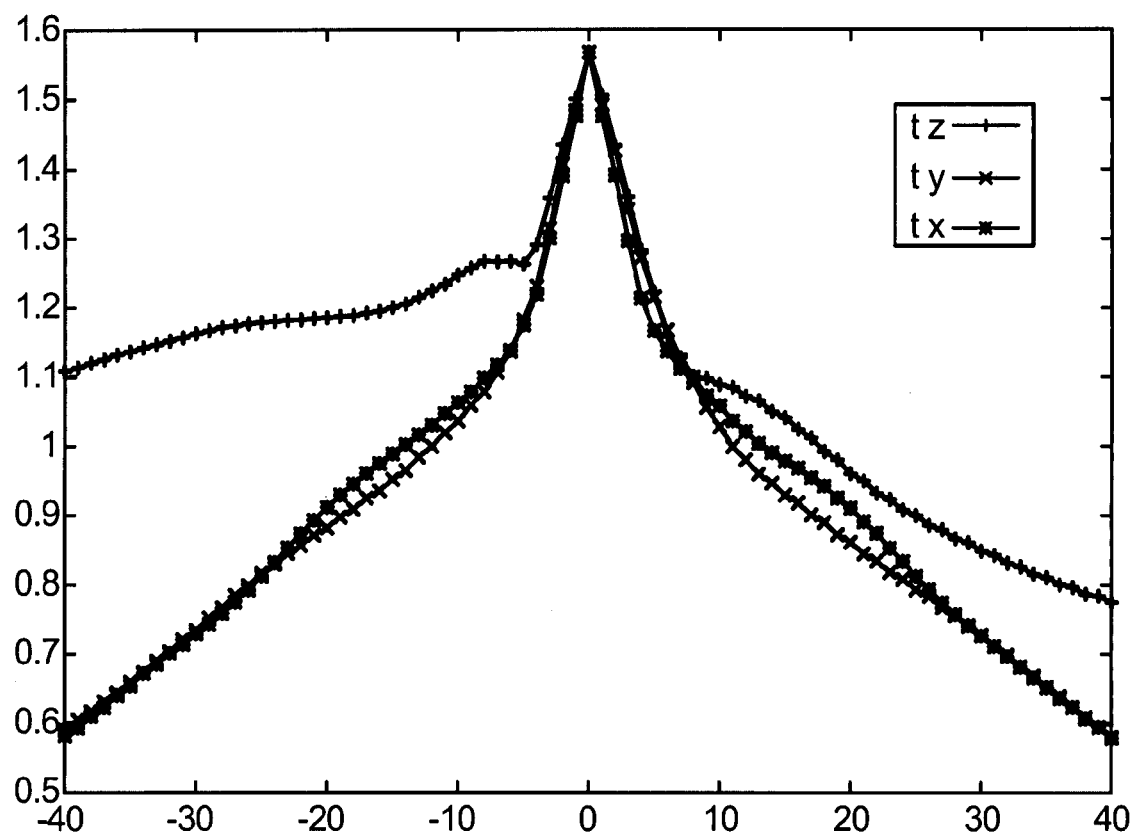
FIG. 2B is a graph showing $\epsilon_a$ with respect to translation.
Figure 2C:
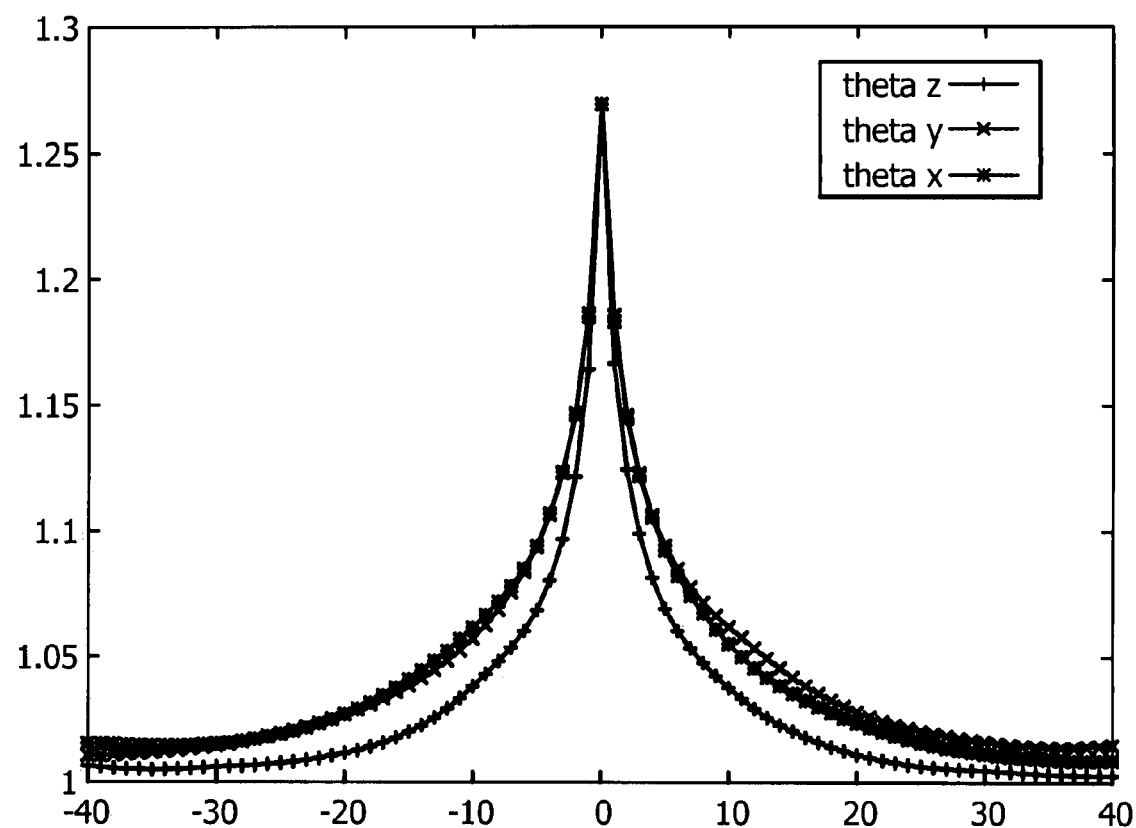
FIG. 2C is a graph showing NMI with respect to rotation.
Figure 2D:
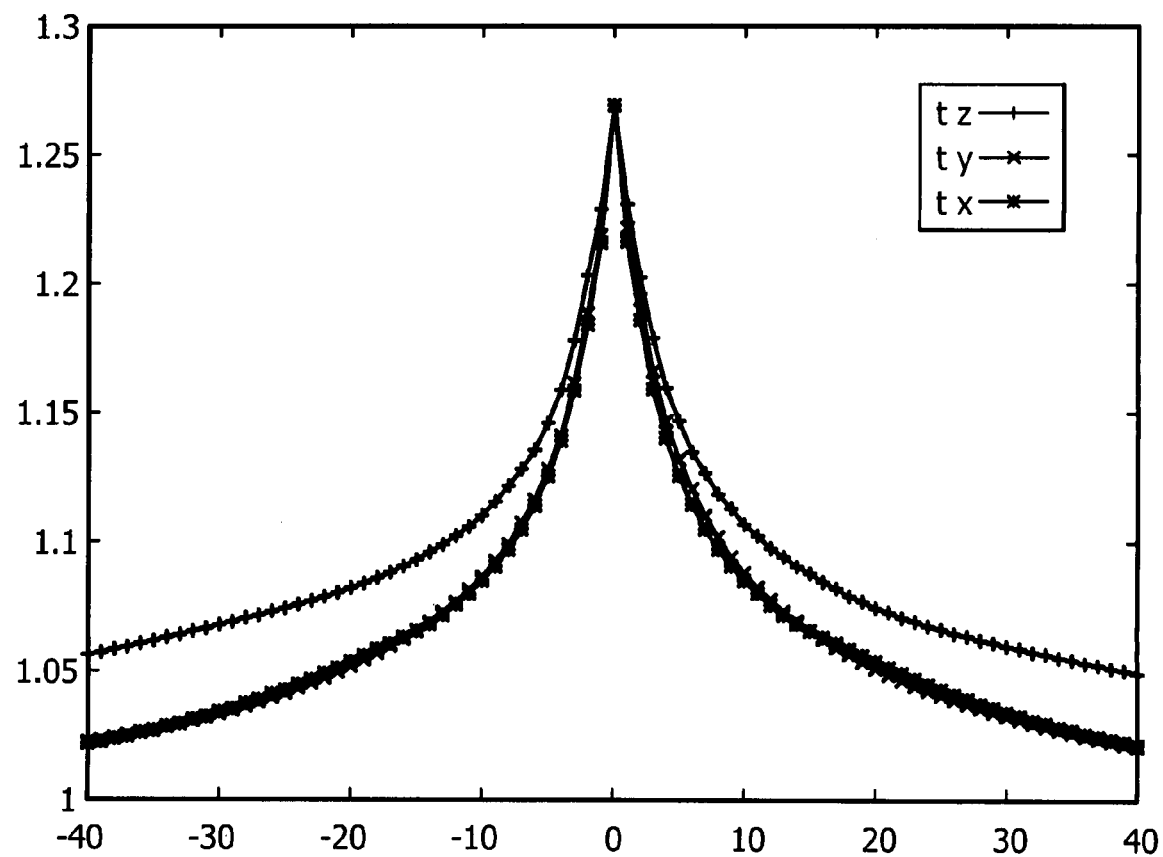
FIG. 2D is a graph showing NMI with respect to translation.

In the first experiment, the value of $\epsilon_a$ and NMI evolves when artificial rotations and translations are applied to one of the volumes. T1 and T2 weighted datasets which were perfectly aligned were used for analysis. Profiles of function $\epsilon_a$ with respect to rotation (FIG. 2A) and with respect to translation (FIG. 2B) are provided. Corresponding profiles for NMI with respect to rotation (FIG. 2C) and translation (FIG. 2D) were also computed for comparison.

Like NMI, $\epsilon_a$ reaches a peak value at 0 and has a large capture range.

Figure 6A:
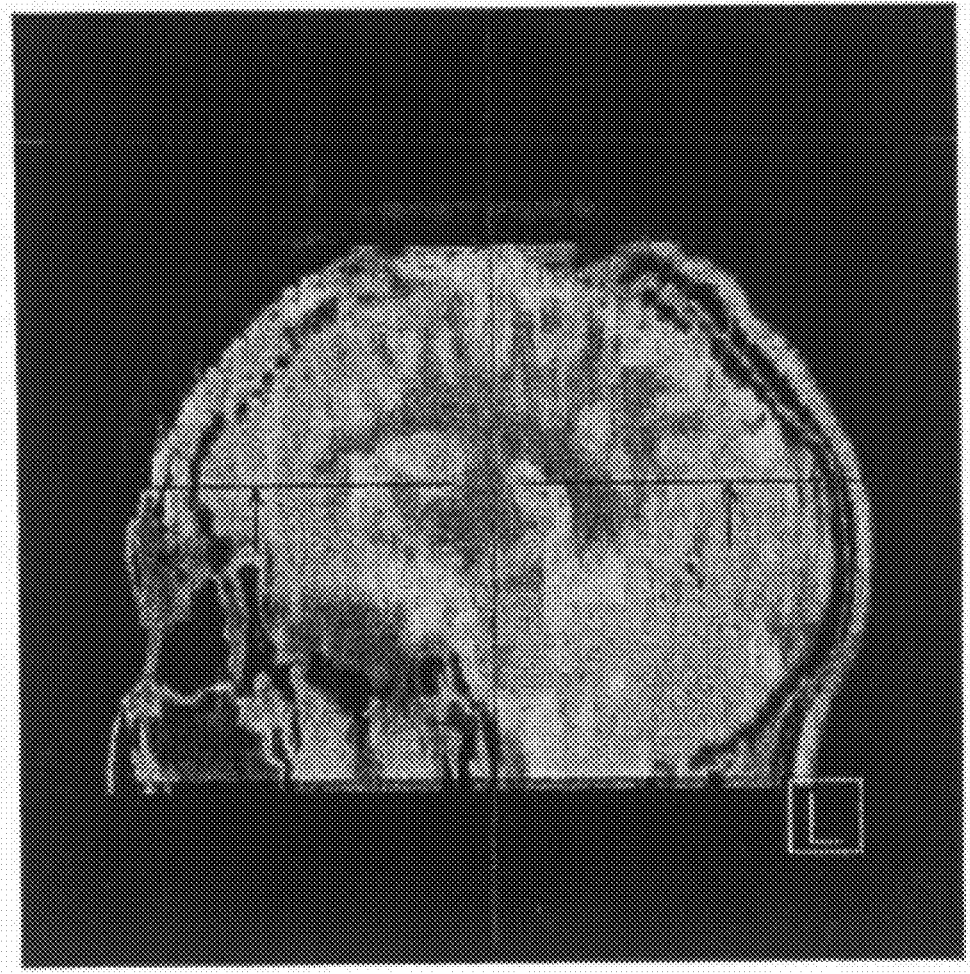
FIG. 6A illustrates a sagittal overlay of set of brain data scans.
Figure 6B:
FIG. 6B illustrates a sagittal overlay of FIG. 6A after alignment.
Figure 6C:
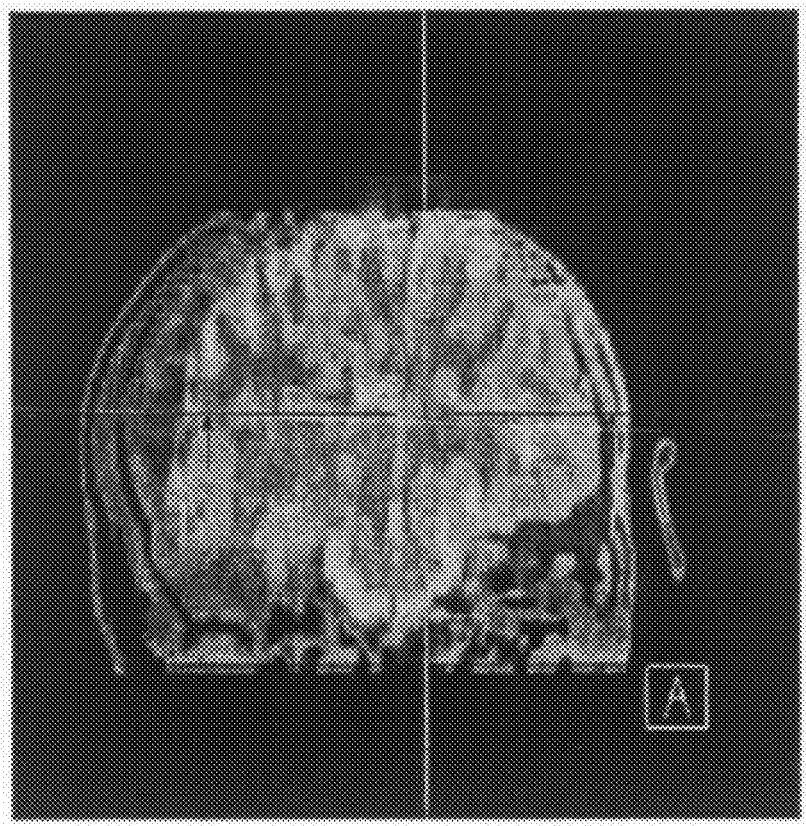
FIG. 6C illustrates a coronal overlay of a set of brain data scans.
Figure 6D:
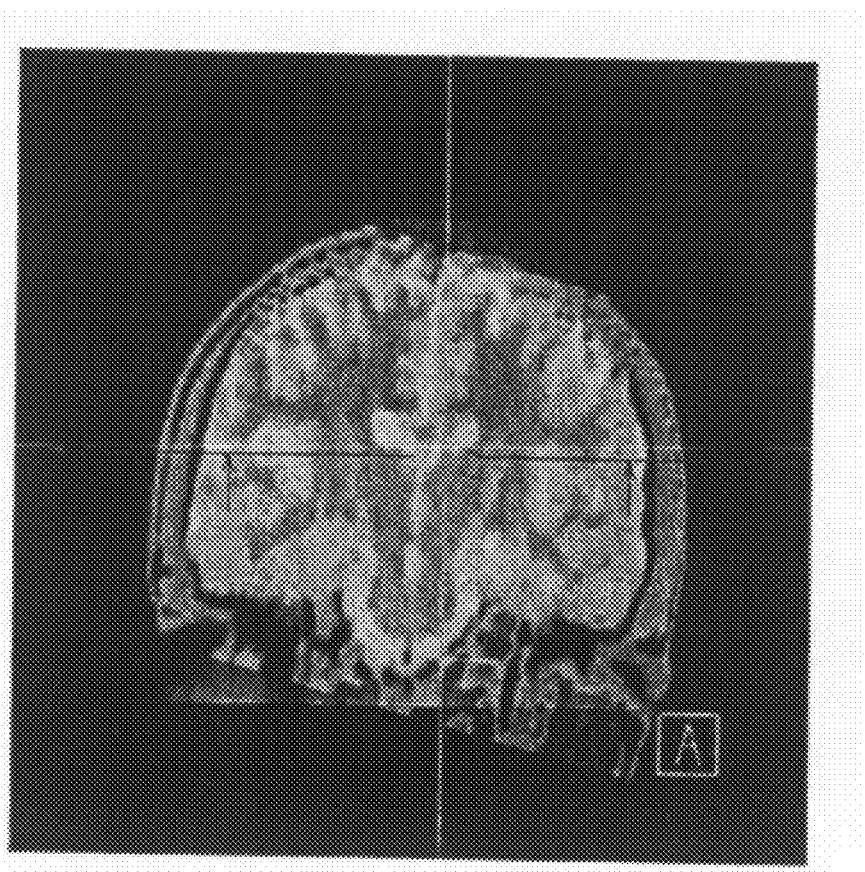
FIG. 6D illustrates a coronal overlay of FIG. 6C after alignment.
Figure 6E:
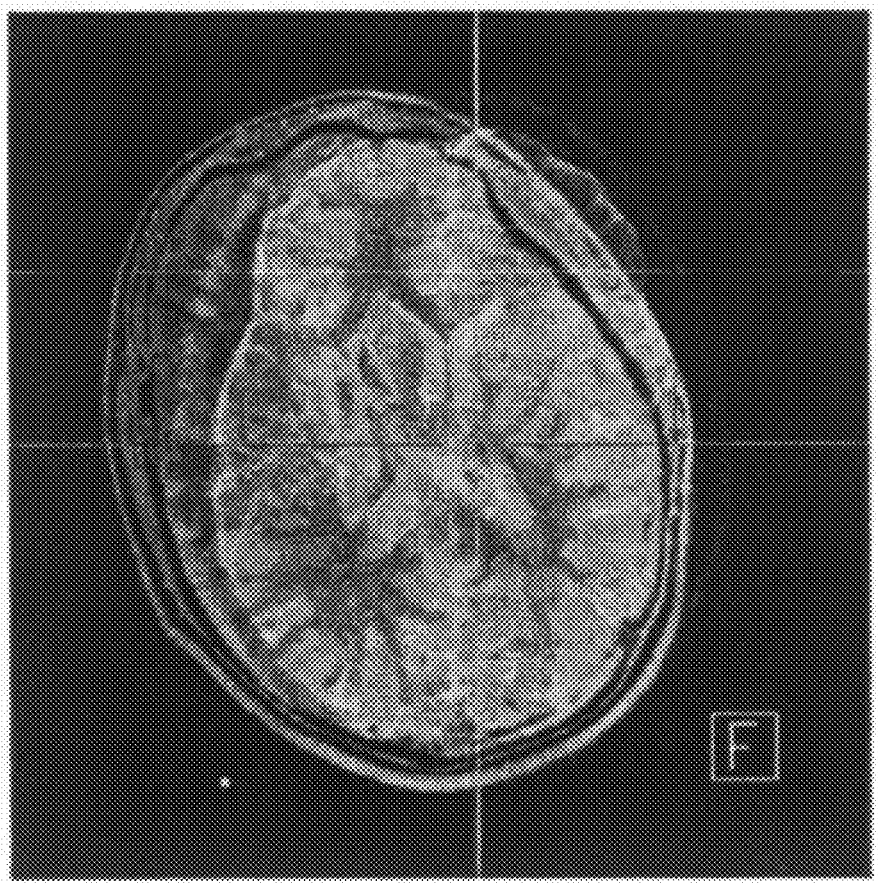
FIG. 6E is an axial overlay of a set of brain data scans.
Figure 6F:
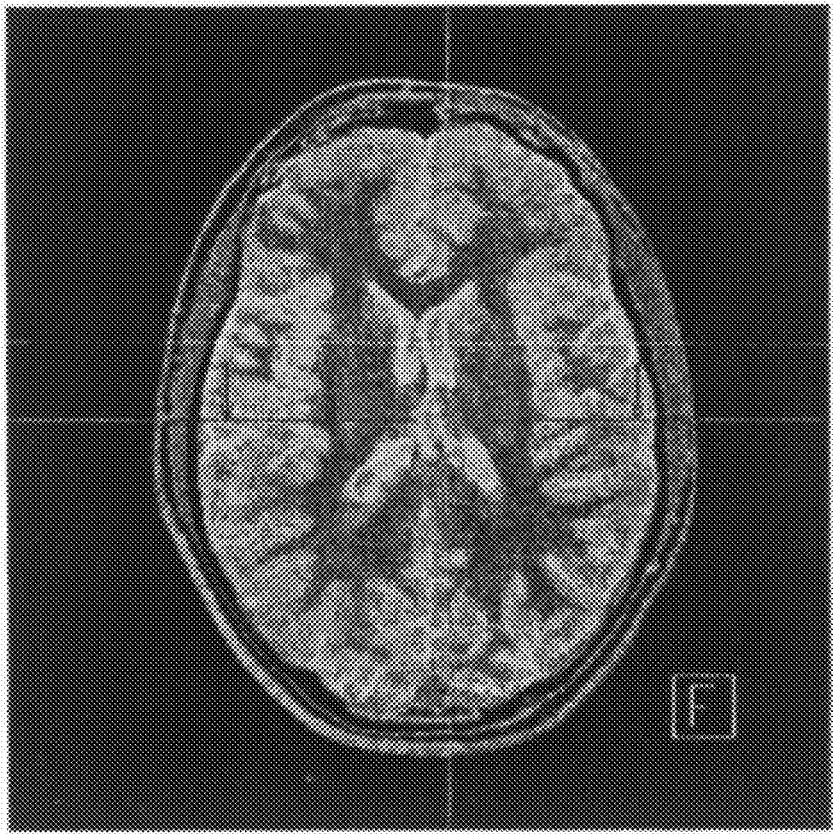
FIG. 6F is an axial overlay of FIG. 6E after alignment

A first qualitative evaluation $\epsilon_a$ is conducted by rigidly aligning the real magnetic resonance data (T2 and T1 weighted scans with a large displacement). The configuration of the images before and after registration are shown in FIGS. 6A to 6F. FIG. 6A illustrates a sagittal overlay, while FIG. 6B illustrates a sagittal overlay after alignment. FIG. 6C illustrates a coronal overlay, while FIG. 6D is a coronal overlay after alignment. FIG. 6E is an axial overlay, while FIG. 6F is an axial overlay after alignment.

Figure 3:
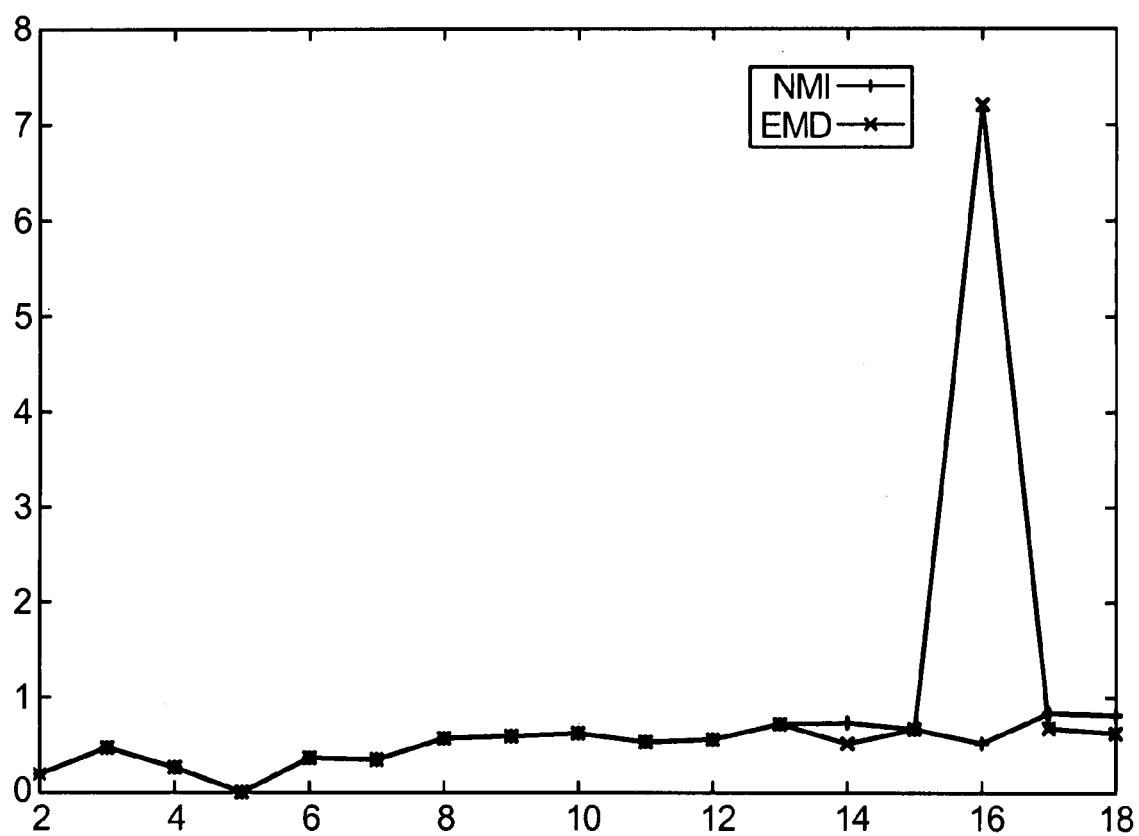
FIG. 3 is a graph of an average registration error for $\epsilon_a$ and NMI.
Figure 4A:
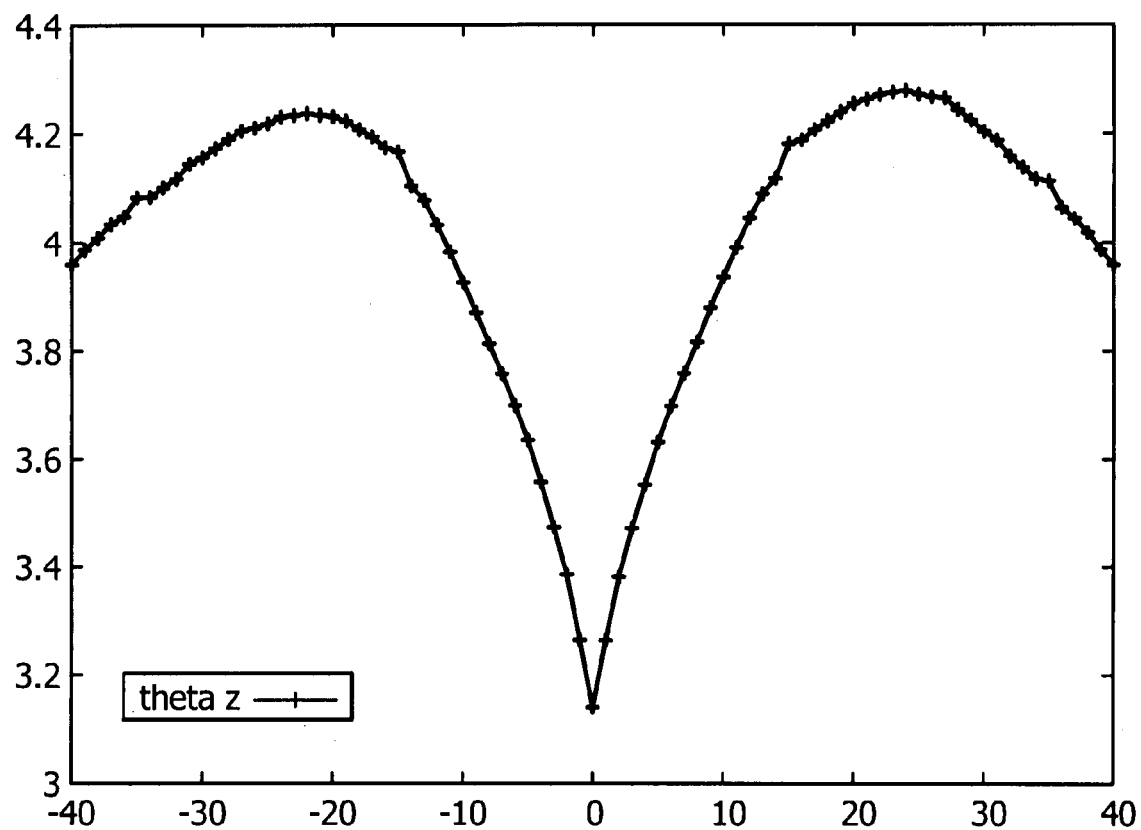
FIG. 4A is a graph of $\epsilon_b$ in gamma compression for distortion applied to a data set.
Figure 4B:
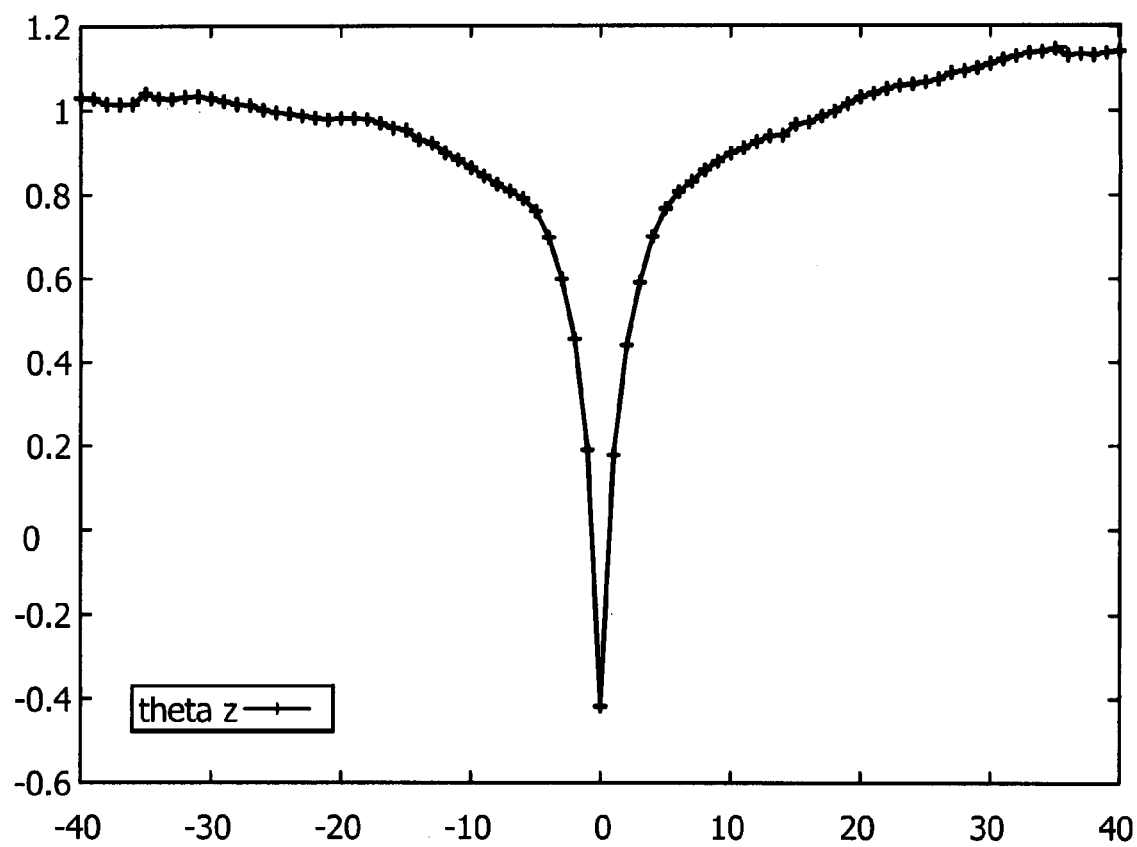
FIG. 4B is a graph of KL in gamma compression for distortion applied to a data set.
Figure 4C:
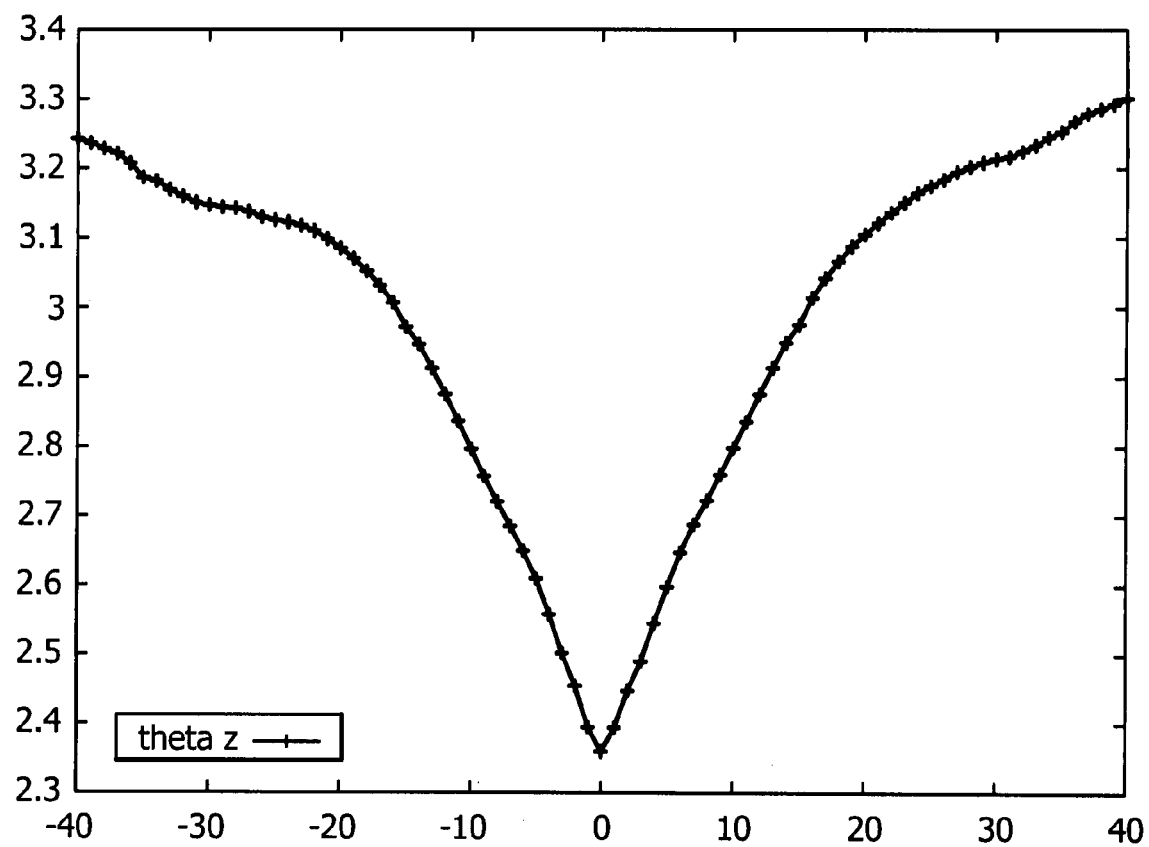
FIG. 4C is a graph of $\epsilon_b$ in gamma expansion for distortion applied to a data set.
Figure 4D:
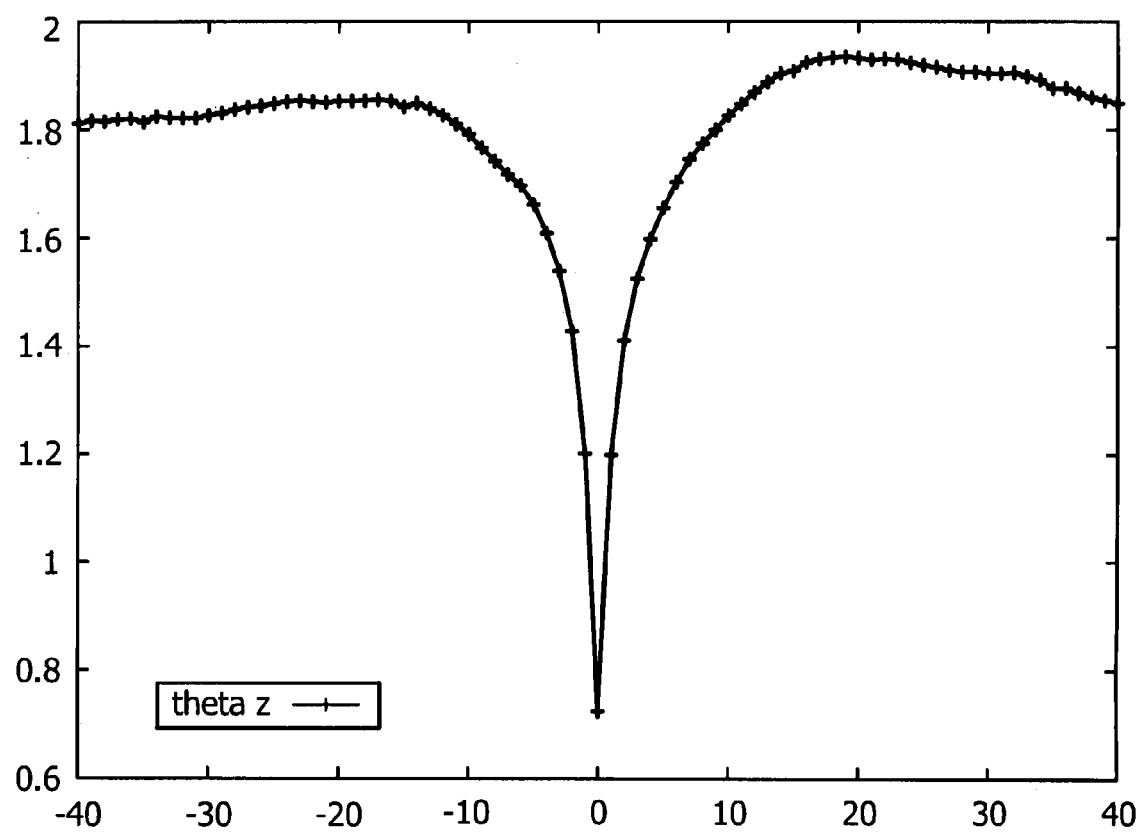
FIG. 4D is a graph of KL in gamma expansion for distortion applied to a data set.
Figure 4E:
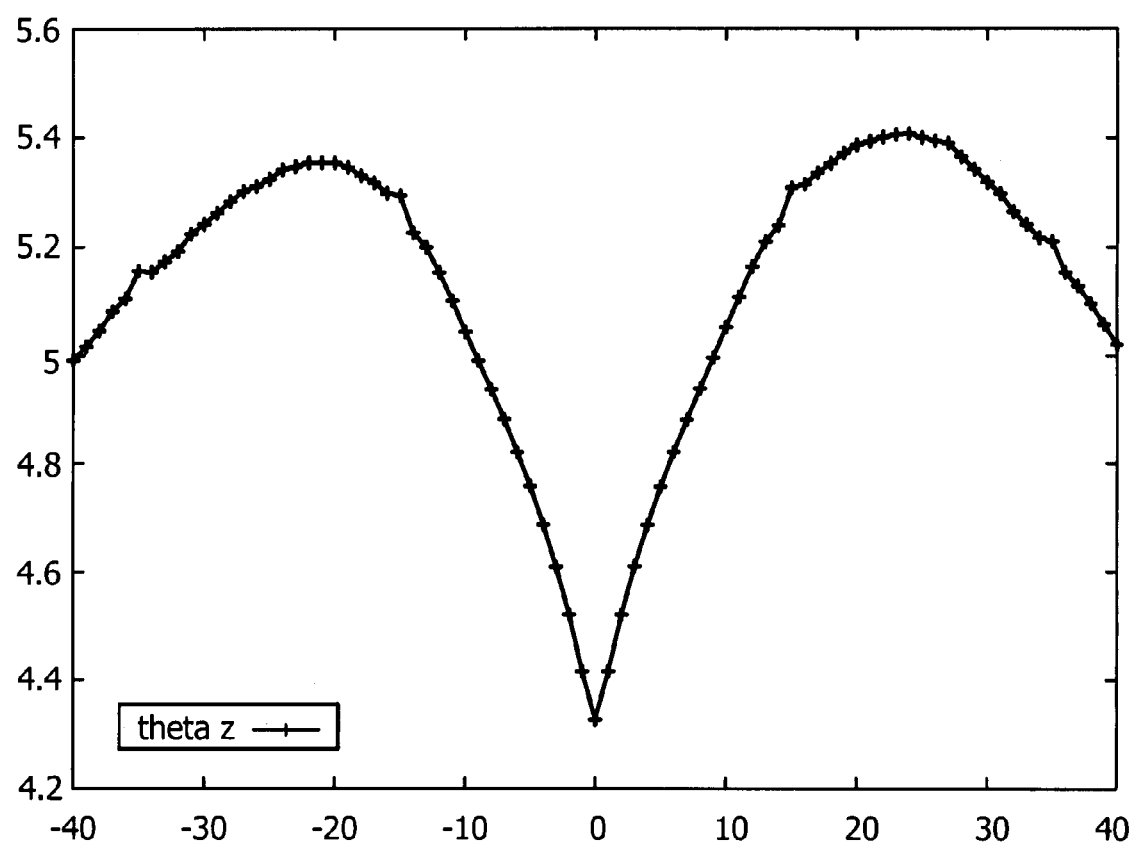
FIG. 4E is a graph of $\epsilon_b$ in gamma compression plus offset for distortion applied to a data set.
Figure 4F:
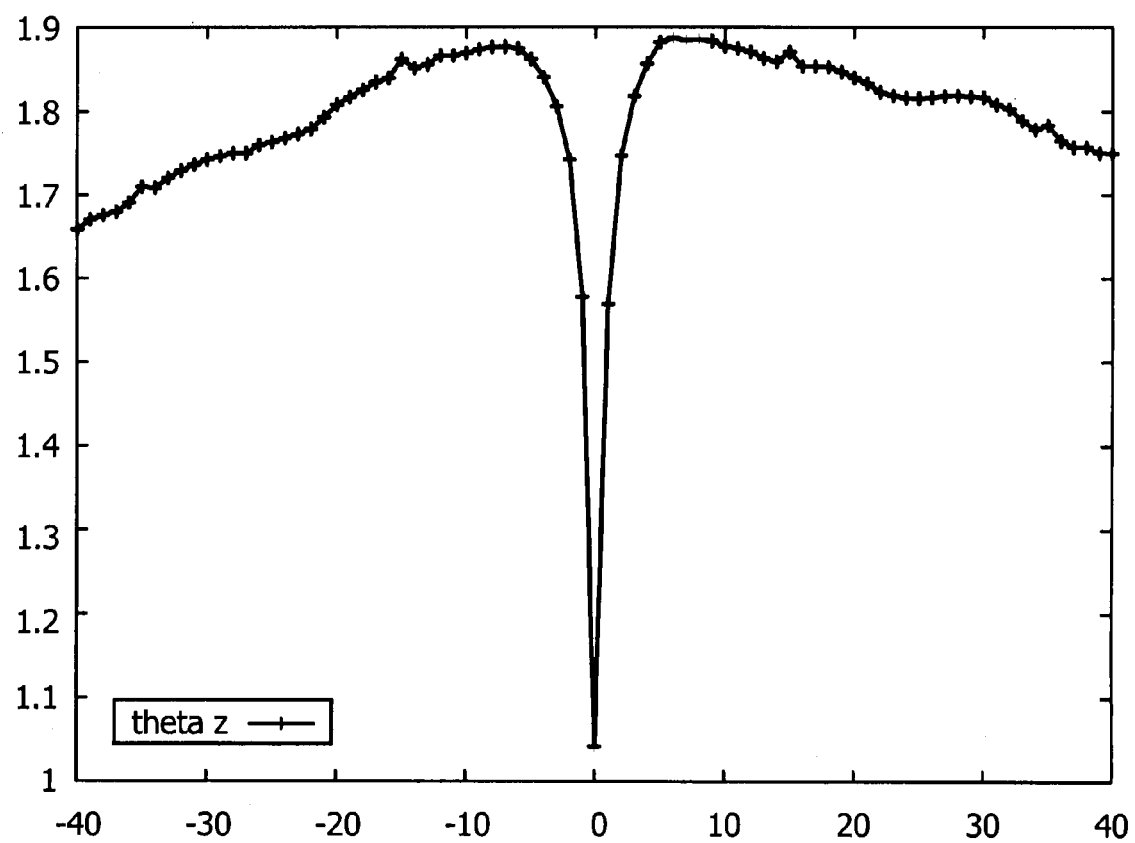
FIG. 4F is a graph of KL in gamma compression plus offset for distortion applied to a data set.

In the next experiment, the average registration errors of $\epsilon_a$- and NMI based rigid registration algorithms for 400 points evenly placed inside the T1- and T2- weighted datasets are computed. The results of the evaluation are presented in FIG. 3. These measurements were obtained by applying 18 known synthetic transformations to the T2 weighted volume. The various levels of rotation and translation ranging approximately between ±10 degrees and ±10 millimeters. The optimization of both measures produces the same solution and success in aligning the image with a sub-voxel accuracy. $\epsilon_a$ outperforms NMI on three datasets, but fails to converge to the correct solution on dataset 16 suggesting a smaller effective capture range.

In the final experiment, a prior distribution from aligned brain images is estimated and compared to the profiles of $\epsilon_b$ and KL with respect to artificial transformations when the intensity values of one of the volumes have been distorted. A gamma compression/expansion operator and an intensity offset are applied to after the intensity profile of the images (with y equal to 0.3 and 1.7, and an offset value equal to 400). These operations are performed before quantization of the data.

In FIGS. 4A to 4F, $\epsilon_b$ is less sensitive than KL to intensity variations. When undergoing gamma compression, the result is particularly significant when combined to the application in an offset, which narrows considerably the capture range of KL.

The present invention provides for an advantage compared to conventional technologies that the method efficiently aligns two image data sets. The alignment of the image data sets allows physicians the capability to not only evaluate a procedures progress with respect to two dimensions, but also in a third dimension, if needed as the alignment is highly accurate. This additional capability, allows for safer and less intrusive medical procedures for patients.

The method and apparatus of the present invention may be used with multiple types of data acquisition systems. An example of this are MRI systems. Other types of scanning may be used and are applicable to use with the method of the present invention. These types of scanning include, for example, x-ray, ultrasound or computed tomography (CT) scanning.

In the foregoing specification, the invention has been described with reference to specific exemplary embodiments thereof. It will, however, be evident that various modifications and changes may be made thereunto without departing from the broader spirit and scope of the invention as set forth in the appended claims. The specification and drawings are accordingly to be regarded in an illustrative rather than in a restrictive sense.

What is claimed is:

1. A method of aligning at least two medical scan images, comprising:
    (a) obtaining a first medical scan image of a quantized object, the first medical scan image having a corresponding first data set;
    (b) obtaining a second medical scan image of the quantized object, the second medical scan image having a corresponding second data set;
    (c) calculating by a computer a joint density with marginals from the first medical scan image and the second medical scan image;
    (d) comparing by a computer the first medical scan image with the second medical scan image using an Earth Mover's Distance between the joint density and the marginals; and
    (e) aligning by a computer the first medical scan image with the second medical scan image with results obtained from the comparing of the first medical scan image with the second medical scan image using the Earth Mover's Distance between the joint density and the marginals.

2. The method according to claim 1, wherein image intensity values of the first data set and image intensity values of the second data set are used in estimating the joint density of the first medical scan image and the second medical scan image.

3. The method according to claim 1, wherein the first medical scan image and the second medical scan image are magnetic resonance images.

4. The method according to claim 1, wherein the first medical scan image and the second medical scan image are computed tomography scan images.

5. A method of aligning at least two images, comprising:
    (a) obtaining a first image of a quantized object, the first image having a corresponding first data set;
    (b) obtaining a second image of the quantized object, the second having a corresponding second data set;
    (c) learning by a computer a joint intensity distribution from a pair of prealigned images; and
    (d) aligning by a computer the first image and the second image by computing an Earth Mover's Distance between their observed joint intensity distribution and the learned joint intensity distribution.

6. The method according to claim 5, wherein the step of aligning the first image and the second image by computing the Earth Mover's Distance between their observed joint intensity distribution and the learned joint intensity distribution is accomplished using an Earth Mover's Distance induced through a formula of $$\epsilon_b(I_1,I_2,T)=\text{EMD}_{L_1}(p_{x1,x2,T},p_0).$$

7. The method according to claim 5, wherein image intensity values of the first data set and image intensity values of the second data set are used in calculating the observed joint intensity distribution of the first image and the second image.

8. The method according to claim 5, wherein the first image and the second image are magnetic resonance images.

9. The method according to claim 5, wherein the first image and the second image are computed tomography scans.

10. A non-transitory program storage device readable by machine, tangibly embodying a program of instructions executable by the machine to perform method steps for aligning at least two medical scan images, comprising:
    (a) obtaining a first medical scan image of a quantized object, the first medical scan image having a corresponding first data set;
    (b) obtaining a second medical scan image of the quantized object, the second medical scan image having a corresponding second data set;
    (c) calculating a joint density with marginals from the first medical scan image and the second medical scan image;
    (d) comparing the first medical scan image with the second medical scan image using an Earth Mover's Distance between the joint density and the marginals; and
    (e) aligning the first medical scan image with the second medical scan image with results obtained from the comparing of the first medical scan image with the second medical scan image using the Earth Mover's Distance between the joint density and the marginals.

11. The device according to claim 10, wherein the first medical scan image and the second medical scan image are magnetic resonance images.

12. The device according to claim 10, wherein the first medical scan image and the second medical scan image are computed tomography scans.

13. A non-transitory program storage device readable by machine, tangibly embodying a program of instructions executable by the machine to perform method steps for aligning at least two medical scan images, comprising:
(a) obtaining a first image of a quantized object, the first image having a corresponding first data set;
(b) obtaining a second image of the quantized object, the second having a corresponding second data set;
(c) learning a joint intensity distribution from a pair of prealigned images; and
(d) aligning the first image and the second image by computing an Earth Mover's Distance between their observed joint intensity distribution and the learned joint intensity distribution.

14. The device according to claim 13, wherein the first image and the second image are magnetic resonance images.

15. The device according to claim 13, wherein the first image and the second image are computed tomography scans.

16. A method of aligning at least two images, comprising:
(a) obtaining a first image of a quantized object, the first image having a corresponding first data set;
(b) obtaining a second image of the quantized object, the second having a corresponding second data set; and
(c) aligning by a computer the first image and the second image by computing an Earth Mover's Distance between their observed joint intensity distribution and the product of its marginals.

17. The method according to claim 1, further comprising: learning a joint intensity distribution from a pair of prealigned images.

18. The method according to claim 1, wherein in the aligning step the first medical scan image with the second medical scan image are aligned by maximizing a factor:

$\epsilon_a(I_1,I_2,T) = \mathrm{EMD}_{L_1}(p_{x1,x2,T}, p_{x1}p_{x2,T})$.

19. A method of aligning at least two images, comprising:
obtaining a first image of a quantized object, the first image having a corresponding first data set;
obtaining a second image of the quantized object, the second having a corresponding second data set;
learning by a computer a joint intensity distribution from a pair of prealigned images; and
aligning by a computer the first image and the second image by computing an Earth Mover's Distance between their observed joint intensity distribution and the learned joint intensity distribution using the Earth Mover's Distance induced through a formula of $\epsilon_b(I_1,I_2,T) = \mathrm{EMD}_{L_1}(p_{x1,x2,T}, p_0)$.

20. The method according to claim 19, wherein the first image and the second image are magnetic resonance images.

21. The method according to claim 19, wherein the first image and the second image are computed tomography scans.

22. The device according to claim 10,
wherein in the aligning step the first medical scan image and the second medical scan image are aligned by maximizing a factor:

$\epsilon_a(I_1,I_2,T) = \mathrm{EMD}_{L_1}(p_{x1,x2,T}, p_{x1}p_{x2,T})$.

23. The device according to claim 13, wherein the first image and the second image are aligned by minimizing a factor:

$\epsilon_a(I_1,I_2,T) = \mathrm{EMD}_{L_1}(p_{x1,x2,T}, p_{x1}p_{x2,T})$.

24. The method according to claim 16
wherein in the aligning step the first image and the second image are aligned by maximizing a factor:

$\epsilon_a(I_1,I_2,T) = \mathrm{EMD}_{L_1}(p_{x1,x2,T}, p_{x1}p_{x2,T})$.

25. The method according to claim 1, wherein the Earth Movers Distance utilizes an $L_1$ ground distance.

26. The method according to claim 5, wherein the Earth Movers Distance utilizes an $L_1$ ground distance.

27. The method according to claim 10, wherein the Earth Movers Distance utilizes an $L_1$ ground distance.

28. The method according to claim 13, wherein the Earth Movers Distance utilizes an $L_1$ ground distance.

29. The method according to claim 16, wherein the Earth Movers Distance utilizes an $L_1$ ground distance.

* * * * *